United States Patent [19]

Coleman

[11] Patent Number: 5,585,098
[45] Date of Patent: Dec. 17, 1996

[54] ORAL ADMINISTRATION OF CHICKEN YOLK IMMUNOGLOBULINS TO LOWER SOMATIC CELL COUNT IN THE MILK OF LACTATING RUMINANTS

[75] Inventor: Marilyn A. Coleman, Columbus, Ohio

[73] Assignee: Ovimmune, Inc., Columbus, Ohio

[21] Appl. No.: 369,310

[22] Filed: Jan. 6, 1995

Related U.S. Application Data

[63] Continuation of Ser. No. 156,540, Nov. 23, 1993, abandoned.

[51] Int. Cl.$^6$ .................. A61K 39/395; A61K 39/40; C07K 16/02; C07K 16/12
[52] U.S. Cl. ............... 424/157.1; 424/150.1; 424/163.1; 424/164.1; 424/165.1; 424/168.1; 424/169.1; 424/170.1; 424/151.1; 424/166.1; 424/802; 424/803; 424/804; 530/388.4; 530/388.6; 530/389.5; 530/390.1; 530/861; 530/388.5
[58] Field of Search ................ 424/804, 802, 424/803, 823, 824, 825, 150.1, 157.1, 163.1, 164.1, 165.1, 168.1, 169.1, 170.1, 151.1, 166.1; 530/388.4, 388.6, 389.5, 390.1, 861, 388.5; 935/107

[56] References Cited

U.S. PATENT DOCUMENTS 3,917,818  11/1975  Botes ..................... 424/163.1
5,080,895  1/1992  Tokoro ..................... 424/157.1

OTHER PUBLICATIONS

Hierlmeier, Inaugural–Dissertation, Tierarztliche Fakultat, Ludwig–Maximilians–Universitat, Munchen, Germany, 1991 (Abstract thereof).

*Primary Examiner*—Ronald B. Schwadron
*Attorney, Agent, or Firm*—Mueller and Smith, LPA

[57] ABSTRACT

A method for lowering somatic cell count in the milk of a lactating ruminant is disclosed. IgY antibodies are first obtained from the egg of a hen which has been actively immunized against one or more mastitis-causing pathogenic organisms by injection with an immunogen containing immunogenic determinants specific to elicit such antibodies. The immunogenic determinant may comprise only a specific portion of the pathogenic organism, e.g., the fimbria of a piliated bacterium. The IgY antibodies are then administered orally to a ruminant in which it is desired to lower milk somatic cell count. Antibody administration may occur during a ruminant's dry period as well as during lactation. In a preferred embodiment, the antigen used in immunization of the hen comprises one or more of *Staphylococcus aureus* and *Streptococcus agalactiae*. The method of this invention has been shown to be efficacious in lowering somatic cell count in dairy cattle.

20 Claims, No Drawings

ORAL ADMINISTRATION OF CHICKEN YOLK IMMUNOGLOBULINS TO LOWER SOMATIC CELL COUNT IN THE MILK OF LACTATING RUMINANTS

This application is a continuation of application Ser. No. 08/156,540, filed Nov. 23, 1993, now abandoned.

BACKGROUND OF THE INVENTION

The present invention relates to mastitis, an extremely important veterinary disease, and to the preparation and administration of egg antibody products which may be used to neutralize a wide variety of systemic pathogens which cause or exacerbate this disease.

The term mastitis refers to inflammation of the mammary gland, regardless of cause. It is characterized by physical, chemical, and usually bacteriological changes in the milk and by pathological changes in the glandular tissue. The most important changes in the milk include discoloration, the presence of clots and the presence of large numbers of leukocytes. Although there is swelling, heat, pain, and induration in the mammary gland in many cases, a large proportion of mastitic glands are not readily detectable by manual palpation or by visual examination of the milk using a strip cup. Because of the very large numbers of such "subclinical" cases, the diagnosis of mastitis has come to depend largely on indirect tests which depend, in turn, on the leukocyte content of the milk. Thus, it is practicable to define mastitis as a disease characterized by the presence of a significantly increased leukocyte content in milk from affected glands. This leukocyte content is commonly referred to as the "somatic cell count," or SCC.

Many infective agents, primarily bacterial but occasionally fungal or protozoal, have been implicated as causes of mastitis. The most common are *Streptococus agalactiae* and *Staphylococcus aureus*, with *Escherichia coli* becoming a significant cause in housed or confined cattle, principally in the northern hemisphere. Other agents include *Streptococcus uberis, Streptococcus dysgalactiae, Corynebacterium (Actinomyces) pyogenes,* Klebsiella spp., *Mycobacterium bovis, Pseudomonas pyocyaneus, Serratia marcescens, Mycoplasma bovis, Nocardia asteroides,* Proteus spp., and *Chlamydia psittaci.*

Infection of each mammary gland occurs via the teat canal, with the infection originating from two main sources, the infected udder and the environment. In dairy cattle and milking goats, the important infections are those which persist readily in the udder, especially *Str. agalactiae* and *Staph. aureus.* The contamination of milkers' hands, washcloths, and milking machine cups by milk from infected quarters may quickly lead to the spread of infection to the teats of other animals. These are commonly referred to as infectious or contagious mastitides.

Bacteria which are normal inhabitants of the environment, such as *E. coli* and *Ps. pyocyaneus,* cause mastitis less frequently but, when they do, the disease is much more resistant to hygienic control measures. Large, zero-grazed herds in feedlots are likely to encounter more hygiene problems than conventionally housed herds. The problems relate mainly to fouling of the udder caused by inadequate or improper bedding in the larger units. Thus, these are known as environmental mastitides.

The frequency of occurrence of mastitis is dependent upon the ability of bacterial agent to set up infection in the mammary tissue. The diferences between bacteria in their ability to set up a mastitic state is dependent on at least two important groups of factors: bacterial characteristics and transmission mechanisms. Bacterial characteristics include the ability of the organism to survive in the cow's immediate environment (i.e., its resistance to environmental influences, including cleaning and disinfection procedures), its ability to colonize the teat duct, its ability to adhere to mammary epithelium and set up a mastitis reaction, and its resistance to antibiotic therapy. Transmission mechanisms are a function of the extent of the infection in the environment (including infected quarters), the efficiency of milking personnel and machinery, milking parlor hygiene, and the susceptibility of the cow. An individual cow's susceptibility, in turn, is a function of the stage of lactation (early lactation, especially the first two months, representing highest susceptibility), the age of the cow (older cows, having had more than four lactations, being more susceptible), the level of inherited resistance (possibly related to teat shape and anatomy of the teat canal), lesions on the teat skin (especially the orifice), and the immunological status of each mammary gland (including prior infections, especially with *Staph. aureus*).

In most countries, surveys of the incidence of mastitis, irrespective of cause, show comparable figures of about 40% morbidity amongst dairy cows and a quarter infection rate of about 25%. The incidence is similar in goats. Surveys of the prevalence of the various infections in cattle show remarkable similarity in different countries. The predominant position of *Str. agatactiae* as a cause of bovine mastitis has been usurped by *Staph. aureus,* especially in areas where the treatment of mastitis with penicillin has been practiced intensively and where machine milking has replaced hand milking. In such areas a relative incidence of *Str. agalactiae,* other streptococci, and *Staph. aureus* of 1:1:2 is a common finding.

Although the prevalence of *Staph. aureus* has been significantly curbed by modem control programs based on teat dipping and dry period treatment, it remains the preeminent cause of subclinical mastitis. Mastitis is said to be subclinical when there is evidence of inflammation, e.g., a high somatic cell count in the milk, without any visible abnormality of the milk or udder. Chronic cases of mastitis, particularly those caused by *Staph. aureus,* are often refractory to treatment while the cow is lactating. For staphylococcal infections in general, a cure rate of 30% is about the best that can be expected. An old adage holds that "once a Staph. cow, always a Staph. cow." Thus, many dairymen choose to cut their losses and simply cull Staph.-positive cows rather than to attempt treatment.

Although mastitis occurs sporadically in all species, it assumes major economic importance only in dairy cattle. In terms of economic loss it is undoubtedly the most important disease with which the dairy industry must contend. In 1992, mastitis infections cost members of the American Dairy Association over $200,000,000. High somatic cell counts in cows result in the loss of approximately 200,000 pounds of milk per cow per year at a financial cost of approximately $288 per cow. Only 10% of the approximately 9,750,000 dairy cows in the United States attain the highest ranking on somatic cell count (below 100,000). A dairyman receives an additional 50 cents per 100-wt. of milk for the highest ranking, i.e., the lowest SCC range. Thus, the insidious presence of subclinical mastitis in a herd can have a devastating effect on milk profits, even in the absence of any external manifestations of disease.

Most estimates show that on the average an affected quarter suffers a 30% reduction in productivity and an affected cow is estimated to lose 15% of its production. Total economic losses caused by mastitis comprise the value of milk production lost, the value of cows lost by premature culling, the value of milk discarded or downgraded, and the cost of treatment and veterinary expenses.

Ordinarily, mastitis is treated either systemically by parenteral injection or locally by intramammary infusion. Parenteral treatment is usually reserved for cases of mastitis in which there is a marked systemic reaction, to control or prevent the development of a septicemia or bacteremia and to assist in the treatment of the infection in the gland. The systemic reaction can usually be brought under control by standard doses of antibiotics or sulfonamides but complete sterilization of the affected quarters is seldom achieved because of the relatively poor diffusion of the antibiotic from the bloodstream into the milk. Parenteral treatment is also used when the gland is badly swollen and intramammary antibiotic is unlikely to diffuse properly. To produce therapeutic levels of antibiotic in the mammary gland by parenteral treatment, it is necessary to use higher-than-normal dose rates, which can alter milk-withholding times, sometimes with disastrous consequences, as discussed infra.

Because of convenience and efficiency, udder infusions have been the preferred method of treatment. Disposable tubes containing suitable drugs in either an aqueous or ointment base are inserted into the teat canal, providing diffusion of drug into the glandular tissue. Strict hygiene is necessary during treatment to avoid the introduction of bacteria, yeasts and fungi into the treated quarters. Diffusion of infused drugs is often impeded by the blockage of lactiferous ducts and alveoli with inflammatory debris. Drug-withholding times are just as applicable to udder infusions as parenterally administered drugs, since these infusions rapidly undergo systemic absorption from the highly vascular udder.

Choice of a suitable drug for the treatment of mastitis is often extremely difficult. In vitro laboratory testing of bacterial sensitivity is not necessarily a justifiable basis for selecting the antibacterial agent to be used in individual cows, and the response to treatment in clinical cases is often unrelated to the results of in vitro sensitivity tests.

In the opinion of the authors of one of the leading texts on large animal veterinary medicine, very little good research and development work has been performed in the field of mastitis prophylaxis and treatment, and most of the products available have been developed with very little scientific support. Attractiveness to the consumer has been placed above efficiency, in the opinion of these authors, resulting in "intramammary preparations containing a battery of antibacterial agents, one or more of a long list of generally unhelpful adjuvants, and inappropriate recommendations about their use, especially with regard to frequency of administration and length of time after treatment for which milk must be withheld from sale." Further, "[t]he indiscriminate and improper use of antibiotics for the treatment of clinical mastitis in lactating cows which has resulted from inaccurate promotion and uninformed use by farmers has meant that the control of mastitis has really received little assistance. Drug-resistant organisms, especially *Staph. aureus*, have been encouraged, and the chances of human consumers of dairy products being exposed to antibiotic residues has been increased." (Blood and Radostits, *Veterinary Medicine: A Textbook of the Diseases of Cattle, Sheep, Pigs, Goats and Horses*, 7th ed., 1989, p. 512).

The effect of antibiotics in milk on the manufacture of dairy products and the development of sensitivity syndromes in human beings is of the utmost consequence. In most countries, the maximum intramammary dose of antibiotics is limited by legislation and the presence of detectable quantities of antibiotics in milk constitutes adulteration. Strict legislation and mandatory milk-testing in the United States have greatly decreased such risk to consumers, but the penalties for milk contamination as a result of inadequate milk-withholding times are enormous and can result in financial disaster for the dairyman and/or veterinarian found to be responsible for such a violation. Since the rate of drug excretion varies among different animals and in the same animal at different points in the lactation period, withholding times specified on drug labels are not always accurate and can lead to inadvertent violation of residue limits. As a result, some dairymen will elect to cull any but the most valuable cows rather than to run the risk of contaminated milk. Even aside from such risk, substantial loss is involved in the discarding of milk during specified withholding times, which can range anywhere from 72 hours for an udder infusion in a lactating cow to 10 days for parenteral antibiotics in long-acting bases.

For the foregoing reasons, there exists a felt need for a mastitis treatment which is not only efficacious, easily administered, and cost-effective, but which is not hampered by the uncertainty and risk of a milk-withholding period. Such a treatment would undoubtedly be enthusiastically received by the dairy industry worldwide.

BROAD STATEMENT OF THE INVENTION

Broadly, the present invention is directed to the use of egg antibody preparations in the prevention and treatment of mastitis, as measured by somatic cell count, in dairy cattle, milking goats, and other susceptible domestic and wild ruminants, such as beef cattle, sheep, deer, milking buffalo, yaks, and the like. IgY antibodies are first obtained from the egg of a domestic fowl hen which has been actively immunized against one or more pathogenic organisms by injection with an immunogen containing immunogenic determinants specific to elicit such antibodies. The procedure for injecting the hens with the immunogens is as described in Fertel et al., "Formation of Antibodies to Prostaglandins in the Yolk of Chicken Eggs," *Biochem. Biophys. Res. Comm.*, 1981, 102: 1028–1033, the disclosure of which is hereby incorporated by reference. The antibodies are then administered orally to a ruminant suffering from, or for the prevention of, mastitis caused or exacerbated by such pathogenic organism or organisms. Administration of the antibodies may occur either during the ruminant's lactation or during its dry period. It is unnecessary to separate the antibodies from the egg yolk, so processing and administration are convenient and inexpensive.

Antibody produced from egg yolks of hens immunized against specific antigens are effective in controlling noxious agents, whether bacterial, fungal, protozoal, viral, toxins, or inflammatory mediators. The immunogenic determinant may comprise only a specific portion of the pathogenic organism, e.g., the fimbria of a piliated bacterium. The method of this invention has been shown to be efficacious in lowering somatic cell count in dairy cattle. In a preferred embodiment, the antigen used in immunization of the hen comprises one or more of *Staphylococcus aureus* and *Streptococcus agalactiae*.

DETAILED DESCRIPTION OF THE INVENTION

It is well known that antibody produced in one species can be used to neutralize the effects of the corresponding antigen in other species. Passive immunization occurs when an individual from one species receives immune protection from antibodies produced in an individual of another species. When, by way of example, the antigen used in immunization of the hen is a bacterium which causes intestinal infectious diseases such as colibacillosis in calves or piglets, the antibody-containing yolk obtained from an egg of the immunized hen in the aforedescribed manner has an activity against the antigen and thus is effective in protection of calves or piglets from attack by the same bacterium used in the immunization. Thus, laying hens may be immunized with a vaccine for pregnant sows in order to obtain high amounts of specific antibodies against porcine enteropathogenic *E. coli* strains. The resultant antibody-containing eggs are then mixed with milk replacer and fed to piglets to treat intestinal colibacillosis. Similarly, hyperimmunized bovine colostrum can be fed orally to calves, piglets, or other neonates to treat intestinal infectious diseases.

In order to be effective against pathogenic agents, specific antibodies must reach their target site immunologically active in order to prevent the germs' adhesion, reproduction, and cell inflammatory mediator release. Heretofore it has never been shown or even suggested that antibody administered by the oral route could be targeted to favorably interfere with specific pathogens or substances in a site remote to the intestine. The crux of the present invention is the discovery that antibody produced in a hyperimmunized yolk model can be delivered orally for systemic delivery to such remote locations as the mammary gland, wherein it chelates mastitis-causing pathogens, preventing inflammation. It is believed that the convenience of oral treatment, coupled with the inexpensive nature of the egg yolk product and its inherent safety, could revolutionize the treatment of this costly disease.

While hyperimmunized colostrum and egg yolks are both effective in providing immunity, chickens possess certain advantages over cows which will be readily apparent to those familiar with both species. Cows are expensive and produce a calf, and thus colostrum, only once a year. The colostrum is only available for 1–2 days and must be refrigerated. In contrast, a hen lays eggs, on average, 7 out of 10 days. Eggs can be stored even at room temperature for several weeks. Once a hen has "learned" to produce antibodies against a specific antigen, it will do so for its entire life, which can span 10 years. Furthermore, the average egg contains 15 ml of yolk having 8 mg/ml of IgG, also referred to as IgY, or "yolk immunoglobulin." This makes the chicken a much more efficient antibody producer than the cow. Chickens produce approximately 20 times more antibody per kg bodyweight than a cow does in colostrum. In addition to chickens, other domesticated and wild fowl may also serve as sources of eggs, e.g., turkeys, ducks, geese, and the like.

The laying hen transfers all antibody isotypes found in the chicken to the egg, i.e., IgY, IgM, and IgA antibodies. The yolk contains only IgY while IgM and IgA are found only in the white. The chicken's serum IgY antibody level is reflected in the egg yolk shortly after a single administration of antibody (about one week). Egg yolk contains 3–25 mg IgY/ml. Depending on its weight, therefore, each egg could provide 40–500 mg IgY.

The advantages of egg yolk antibodies are numerous. Chicken antibodies do not react with mammalian complement, Fc receptors, protein A or protein G. Yolk antibodies show great acid and heat resistance. Extraction of yolk antibodies can be performed even on a large scale without costly investment. Concentrating the antibody from egg yolk is a relatively straightforward process. The antibody is not harmed by pasteurization. The FDA regards egg antibody as a food rather than a drug and has granted GRAS (generally accepted as safe) status thereto. Thus, there would be no problem with consumption of milk from dairy cattle treated with egg yolk antibodies, and no mandatory milk-withholding period, in sharp contrast to antibiotics.

The techniques for immunization of a hen against selected antigens are well-known to those in the art. Briefly, immunization may be performed by inoculation with the antigen by any appropriate route such as subcutaneous, intraperitoneal, intramuscular, or intravenous injection, or oral administration. The preferred method of immunization is by injection, preferably subcutaneously on the neck. Preferably a suitable adjuvant is administered in conjunction with the antigen to enhance the immunization. An adjuvant useful for this purpose is a water-in-oil emulsion adjuvant such as complete Freund's adjuvant (CFA). It has been found that the use of a suitable adjuvant is highly effective in maintaining a high antibody titer in the eggs of an immunized hen for a prolonged period, thereby making it possible to produce the desired antibody-containing substance efficiently. The dose of the antigen is determined depending on the type of the antigen and adjuvant and the administration route in such a manner that an immune status is induced in the hen without development of excessive antigen toxicity.

Usually within a few weeks following the initial immunization (inoculation), the hen becomes sensitive to the antigen, i.e., immunized against the antigen. A specific antibody against the antigen is produced within the body of the hen, and an egg laid by the hen contains the specific antibody. The presence and the titer level of the specific antibody against the antigen in the hen and in eggs of the hen can be confirmed by a number of methods known to those skilled in the art of immunological tests.

After the initial immunization of the hen against the antigen, one or more boosters at an appropriate dose level may be administered in order to maintain a high antibody titer in the hen. Again, in each booster administration, a suitable adjuvant may be used in conjunction with the antigen. The interval between the initial immunization and the first booster administration and between individual booster administrations depends on the specific characteristics of the antigen and is preferably at least two weeks.

After it is confirmed that an adequate titer of the desired specific antibody is present in an egg laid by the immunized hen, an egg laid by the hen is collected and, if necessary, stored until use. Conveniently, a plurality of eggs laid by one or more hens which have been immunized against the same antibody are collected and processed together to produce the desired substance which contains the antibody. Since most antibodies are contained in the yolk of an egg, the yolk is usually separated from the collected egg or eggs for use in the production of the desired antibody.

The adhesion to the host is an important factor of primary virulence. A variety of adhesive structures, broadly referred to as adhesins or lectans, on the surfaces of microorganisms serve to bind them to complementary adhesive structures on the surfaces of host cells known as receptors. The cell receptor is comprised primarily of glycoproteins or glycolipids, two types of complex carbohydrates in which sugars are linked to proteins and lipids, respectively. Several thousand such receptors have been identified. The adhesin of a pathogenic organism is now known to be a lectan once thought to be found only in plants. These are found on the surface of pathogens, strategically positioned to combine with very specific carbohydrate receptors of the susceptible cell. Lectans have been identified on toxins, viruses, bacteria, and fungi. Some pathogenic organisms have also developed proteinaceous surface structures, such as the fimbriae, or pili, of *E. coli*. Such structures play a role in the interaction of the organism with the glycoprotein receptor of host cells. Adhesion of the pili lectan to the host cell surface's glycoprotein receptor or basement membranes serves as an essential first step in the pathogenesis of disease. If there is no adhesion, there is no disease.

Antibody can be raised against certain portions of pathogenic organisms rather than the organisms in entirety. For example, it has been found that antibody raised against the specific adhesin of a pathogenic organism, e.g., the pilus in fimbriated bacteria such as *E. coli*, is extremely effective in preventing disease caused by that organism. This could prove beneficial in the treatment of coliform mastitis caused by *E. coli*, wherein antibody could be raised against a specific pilus rather than the organism in entirety.

The newly discovered systemic effect of IgY relates to the absorption or translocation of fragments of orally administered antibody from the intestine into circulation. The IgY molecule is disassembled by naturally occurring enzymes in the intestine into binding fragments, which comprise peptides of the highly variable portion of the terminal domain of the antibody. Peptides which are seven to eight amino acids long are known to be absorbed. Once in the circulation, these fragments randomly search out a pathogen with the matching lectan and neutralize it by binding to that site. The adhesins are then rendered incapable of binding to a susceptible cell receptor. The constant, or Fc, portion of IgY is left in the intestine. Only peptides of the highly variable portion of the antibody, the Fab chain, are taken into circulation. These Fab moieties, unlike the Fc portion, do not elicit an allergic reaction, presumably because they are either too small or are unrecognized as foreign for some other reason. These Fab moieties can be added to the terminal end of the host's circulating globulin, wherein they are hidden from destruction but available for neutralization.

The following Example demonstrates how the present invention has been practiced, but should not be construed as limiting. In this application, all citations are expressly incorporated herein by reference.

EXAMPLE

The objective of this experiment was to determine the effect on a screened milking herd of administering hyperimmune yolk containing antibodies of bacteria known to cause high somatic cell counts.

Twenty-four cows, having no visible lesions, were tested for somatic cell count. Four of those cows were at the extremes of somatic cell counts (too low or too high) and were eliminated from the experiment. Seven days before treatment, the selected cows were tested for somatic cell count again. This process was continued until there were 18 cows in the experiment. These cows were then divided into 3 equal groups of 6 cows each.

Hyperimmune egg preparation was then begun. Seventeen-week-old pullets were allowed 5 days to acclimate to new surroundings. The pullets were then injected with the specific antigen groups *Staphylococcus aureus* and *Streptococcus agalactiae*. (Group B). The injections were prepared by growth of the bacteria in Tryptic Soy Broth (TSB), cultured for 24 hours, then concentrated by centrifuge. The concentration was resuspended in 1% formulation, then incubated a second time for 24 hours at 35° F. The resulting broth was concentrated by centrifuge and washed twice in phosphate buffer, then resuspended in a water solution. The injection mixture was lyophilized before sent to inoculate hens. A sample of the injection was plated out on a blood agar plate to check for viable organisms and/or bacteria. The injections were repeated a second and third time at 2–3 week intervals.

Eggs were collected from the group and stored until the desired number of eggs were collected to complete the experiment (12 days). Naive eggs were obtained from a local supermarket to provide control eggs. All hyperimmune eggs were opened and whites removed. Eggs were placed in a large vessel and mixed to obtain a homologous sample to use for the hyperimmune eggs. The same protocol was used to obtain the naive yolk samples. Egg yolks were divided into daily doses and frozen to below 0 F. They were then shipped to the location of the experiment without thawing. Daily groups of eggs were removed from storage and subdivided to account for equal portions of eggs, either hyperimmune or naive, for each cow each day of the 10 days of the experiment.

When 540 hyperimmune eggs had been collected, cows were tested as described, supra, and the experiment was begun. Hyperimmune eggs were pooled and divided into ten equal portions. Each portion was then subdivided into six equal portions. These portions were marked according to day and cow number for experimental purposes. Next, 540 control eggs, obtained commercially from a local source, were opened and processed in the same manner as the hyperimmune eggs. During the experiment, the daily samples of frozen hyperimmune and control yolks were ground in a meat grinder.

Each of the three equal groups of cows was provided with the same total amount of protein each day. Group A, the first control group, was fed the eggs collected from a commercial source with no special antibody titers. Group B was fed hyperimmune yolk equivalent to 3.0 ounces of dry egg product. Group C, the second control group, was fed soybeans as a protein source. The yolks or soybeans were mixed with the feed for the evening feeding only.

The results of the experiment are shown in Table 1. Cows from the control groups increased in somatic cells counts by either 25%, for naive egg supplementation, or 28%, for soybean supplementation, whereas the hyperimmune treated group decreased in somatic cell count by 28% for a net difference from the controls of greater than 50%.

It was not expected that all of the controls would increase in somatic cell counts. This experiment was conducted in the upper midwestern United States during the 1993 floods. Because of poor environmental conditions, i.e., wet fields, almost all of the dairy herds in this region increased in somatic cell counts. The average increase for the state of Minnesota was 28%, which matches closely with the control data. In fact, there were 20 out of 26 herds in this particular geographic region that did not pass the somatic cell count tests for the two months in which this experiment was conducted. The fact that the hyperimmune egg yolk effected a decrease in somatic cell count, especially one of this magnitude, is particularly noteworthy in view of these unusually diffficult circumstances.

TABLE 1

| Cow No. | 1st Count 13 Days before Treatment | 2nd Count 5 Days before Treatment | Percent Increase 1st to 2nd | Average of 2 Counts | Final Count 3 Days after Treatment | Percent Increase from Average | Percent Increase from 2nd Count |
|---|---|---|---|---|---|---|---|
| 1A | 52,000 | 41,000 | −21.15 | 46,500 | 156,000 | 235.48 | 280.49 |
| 2A | 72,000 | 98,000 | 36.11 | 85,000 | 147,000 | 72.94 | 50.00 |
| 3A | 71,000 | 63,000 | −11.27 | 67,000 | 63,000 | 5.97 | 0.00 |
| 4A | 135,000 | 66,000 | −51.11 | 100,500 | 290,000 | 188.56 | 339.39 |
| 5A | 365,000 | 356,000 | −2.47 | 360,500 | 360,000 | −0.14 | 1.12 |
| 6A | 233,000 | 897,000 | 284.98 | 565,000 | 615,000 | 8.85 | −31.44 |
| 1B | 34,000 | 22,000 | −35.29 | 28,000 | 17,000 | −39.29 | −22.73 |
| 2B | 61,000 | 102,000 | 67.21 | 81,500 | 69,000 | −15.34 | −32.35 |
| 3B | 199,000 | 100,000 | −49.75 | 149,500 | 114,000 | −23.75 | 14.0 |
| 4B** | 225,000 | 257,000 | 14.22 | 241,000 | 1,507,000 | 525.31 | 486.38 |
| 5B | 452,000 | 454,000 | 0.44 | 453,000 | 372,000 | −17.88 | −18.06 |
| 6B | 356,000 | 930,000 | 161.24 | 643,000 | 212,000 | −67.03 | −77.20 |
| 1C | 58,000 | 60,000 | 3.45 | 59,000 | 54,000 | −8.47 | −10.00 |
| 2C | 84,000 | 60,000 | −28.57 | 72,000 | 114,000 | 58.33 | 90.00 |
| 3C | 72,000 | 206,000 | 186.11 | 139,000 | 155,000 | 11.51 | −24.76 |
| 4C** | 206,000 | 433,000 | 110.19 | 319,500 | 2,224,000 | 596.09 | 413.63 |
| 5C | 648,000 | 205,000 | −68.36 | 426,500 | 885,000 | 102.81 | 321.95 |
| 6C | 680,000 | 1,049,000 | 54.26 | 864,500 | 1,144,000 | 32.33 | 9.06 |

**Cows tested positive for Mastitis

I claim:

1. A method for lowering somatic cell count in the milk of a lactating ruminant infected with a mastitis-causing organism, which comprises the steps of:
   (a) injecting a fowl hen with an immunogen containing immunogenic determinants specific to elicit IgY antibodies against said mastitis-causing organism; and
   (b) orally administering said IgY antibodies to said infected lactating ruminant.

2. The method of claim 1, wherein said mastitis-causing organism is selected from the group consisting of *Staphylococcus aureus, Streptococcus agalactiae, Escheria coli, Corynebacterium (Actinomyces) pyogenes, Mycoplasma bovis, Pseudomonas pyocyaneus, Streptococcus uberis, Streptococcus dysgalactiae, Mycobacterium bovis,* Klebsiella spp., *Serratia marcescens, Nocardia asteroides,* Proteus spp., and *Chlamydia psittaci.*

3. The method of claim 2, wherein said mastitis-causing organism is selected from the group consisting of *Staphylococcus aureus, Streptococcus agalactiae, Escheria coli, Corynebacterium (Actinomyces) pyogenes,* and *Mycoplasma bovis.*

4. The method of claim 1, wherein said lactating ruminant is selected from the group consisting of dairy cattle, milking goats, beef cattle, sheep, deer, milking buffalo, and yaks.

5. The method of claim 4, wherein said lactating ruminant is selected from the group consisting of dairy cattle and milking goats.

6. The method of claim 1, wherein said fowl hen is selected from the group consisting of chicken, duck, goose, and turkey.

7. The method of claim 6, wherein said fowl hen is a chicken.

8. The method of claim 1, wherein said IgY antibodies are obtained from the yolk of an egg without fractionation thereof.

9. The method of claim 8, wherein the IgY antibodies are in the form of a powder obtained by stirring the yolk of said egg into an emulsion and drying the emulsion to form a powder.

10. The method of claim 5, wherein said mastitis-causing organism is selected from the group consisting of *Staphylococcus aureus* and *Streptococcus agalactiae.*

11. The method of claim 1, wherein the immunization of said fowl hen is performed by administration of the immunogen in conjunction with a water-in-oil emulsion adjuvant.

12. A method for treating mastitis, as determined by measurement of somatic cell count in a ruminant, caused or exacerbated by one or more pathogenic organisms in said ruminant, which comprises the steps of:
   (a) injecting a fowl hen with an immunogen containing immunogenic determinants specific to elicit IgY antibodies against said one or more pathogenic organisms; and
   (b) orally administering said IgY antibodies to said ruminant.

13. The method of claim 12, wherein said one or more pathogenic organisms is selected from the group consisting of *Staphylococcus aureus, Streptococcus agalactiae, Escheria coli, Corynebacterium (Actinomyces) pyogenes, Mycoplasma bovis, Pseudomonas pyocyaneus, Streptococcus uberis, Streptococcus dysgalactiae, Mycobacterium bovis,* Klebsiella spp., *Serratia marcescens, Nocardia asteroides,* Proteus spp., and *Chlamydia.*

14. The method of claim 13, wherein said one or more pathogenic organisms is selected from the group consisting of *Staphylococcus aureus, Streptococcus agalactiae, Escheria coli, Corynebacterium (Actinomyces) pyogenes,* and *Mycoplasma bovis.*

15. The method of claim 12, wherein said ruminant is selected from the group consisting of dairy cattle and milking goats.

16. The method of claim 15, wherein said fowl hen is a chicken.

17. The method of claim 12, wherein said IgY antibodies are obtained from the yolk of an egg without fractionation thereof.

18. The method of claim 12, wherein the IgY antibodies are in the form of a powder obtained by stirring the yolk of an egg into an emulsion and drying the emulsion to form a powder.

19. The method of claim 16, wherein said one or more pathogenic organisms is selected from the group consisting of *Staphylococcus aureus* and *Streptococcus agalactiae.*

20. The method of claim 12, wherein the immunization of said fowl hen is performed by administration of the immunogen in conjunction with a water-in-oil emulsion adjuvant.

* * * * *